United States Patent [19]

Wiesner et al.

[11] Patent Number: 5,348,537
[45] Date of Patent: Sep. 20, 1994

[54] CATHETER WITH INTRALUMINAL SEALING ELEMENT

[75] Inventors: Steven P. Wiesner; Ketan P. Muni, both of San Jose, Calif.

[73] Assignee: Advanced Cardiovascular Systems, Inc., Santa Clara, Calif.

[21] Appl. No.: 913,859

[22] Filed: Jul. 15, 1992

[51] Int. Cl.⁵ .............................................. A61M 29/02
[52] U.S. Cl. ...................................... 604/96; 604/256; 604/265; 606/194
[58] Field of Search .................... 604/96, 99, 164, 165, 604/167, 256, 265; 606/192, 194

[56] References Cited

U.S. PATENT DOCUMENTS

| | | | |
|---|---|---|---|
| 4,798,597 | 1/1989 | Vaillancourt | 604/265 |
| 4,994,047 | 2/1991 | Walker et al. | 604/265 |
| 4,998,923 | 3/1991 | Samson et al. | 604/96 |
| 5,015,238 | 5/1991 | Solomon et al. | 604/164 |
| 5,104,389 | 4/1992 | Deem et al. | 604/167 |

Primary Examiner—John D. Yasko
Assistant Examiner—Anthony Gutowski
Attorney, Agent, or Firm—Crosby, Heafey, Roach & May

[57] ABSTRACT

A sealing element for dilatation and other inflatable catheters which is formed of a polymer matrix having a bearing surface and having incorporated, at least in the portion of the matrix forming the bearing surface, a lubricous material which swells upon contact with an aqueous based liquid. The bearing surface is adapted to engage the surface of a movable member such as a guidewire when the bearing surface expands from contact with aqueous based liquid. This engagement seals the interface between the movable member and the sealing element and prevents the passage of significant amounts of liquid through the interface between these elements.

11 Claims, 2 Drawing Sheets

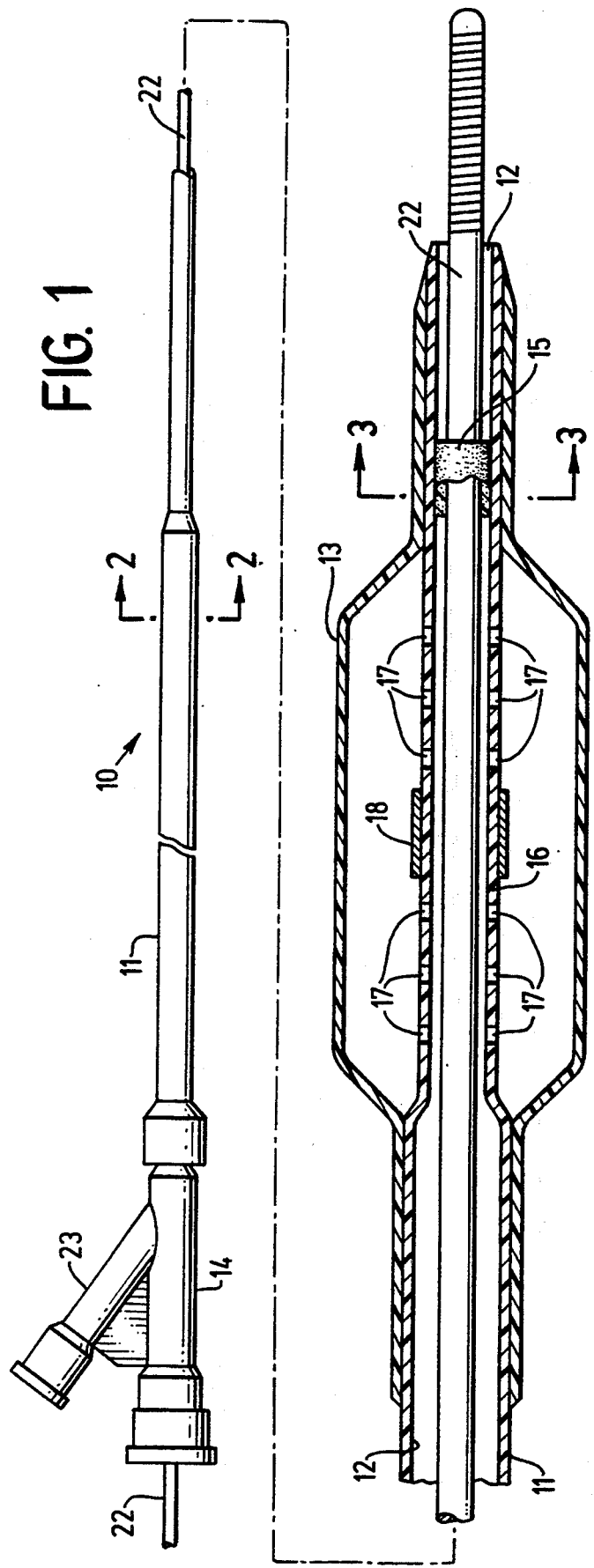
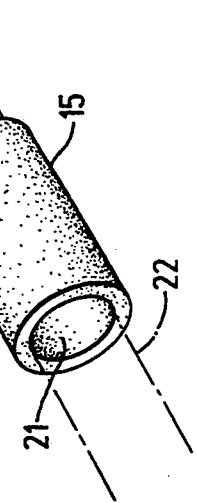
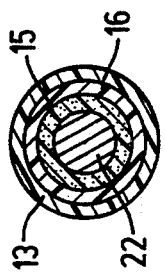
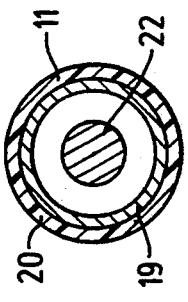

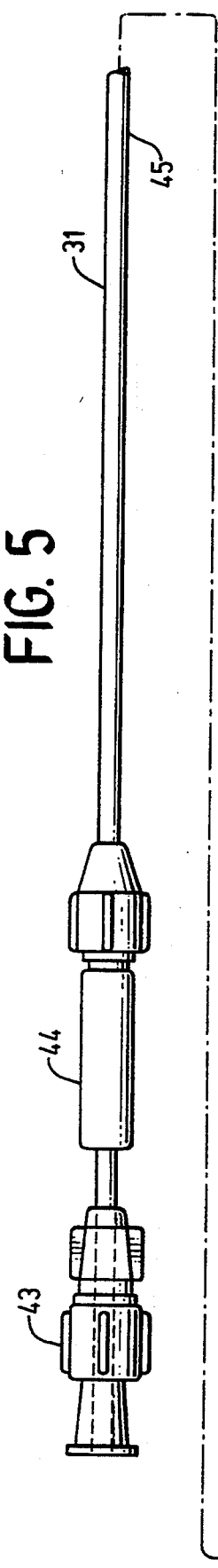
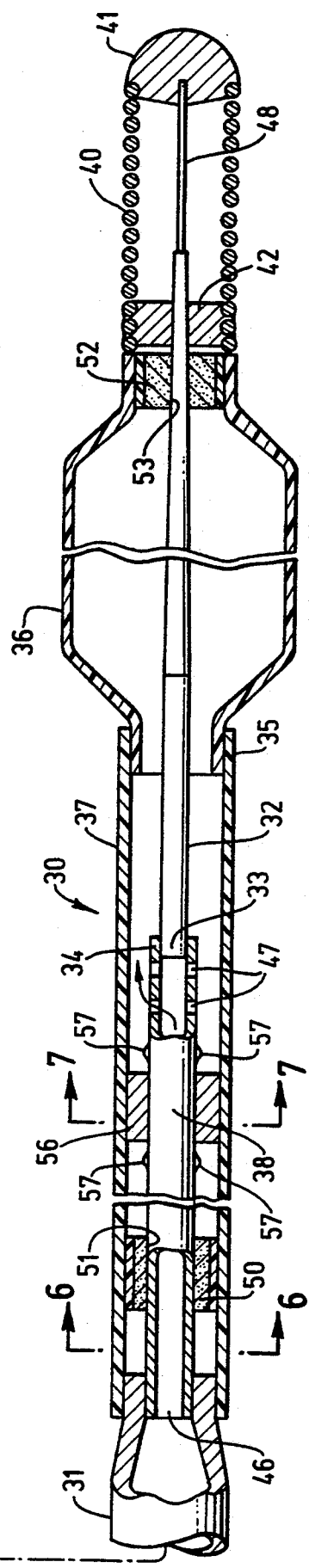
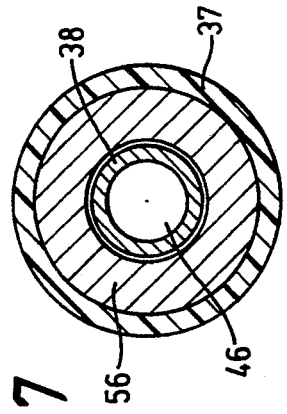
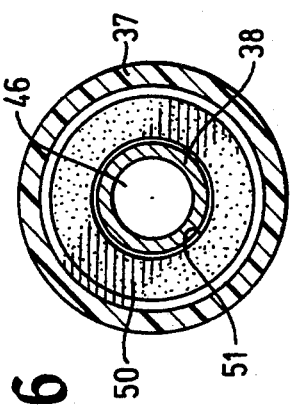
FIG. 5
FIG. 7
FIG. 6

CATHETER WITH INTRALUMINAL SEALING ELEMENT

BACKGROUND OF THE INVENTION

The present invention is directed to intraluminal catheters which are suitable for procedures such a percutaneous transluminal coronary angioplasty (PTCA) procedures.

PTCA is a widely used procedure for the treatment of coronary heart disease. In this procedure, a balloon dilatation catheter is advanced into the patient's coronary artery and the balloon on the catheter is inflated within the stenotic region of the patient's artery to open up the arterial passageway and increase blood flow through the artery. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries. The catheter is advanced within the selected artery until the preshaped distal tip of the guiding catheter is disposed within the aorta adjacent the ostium of the desired coronary artery. The guiding catheter is twisted or torqued from the proximal end, which extends out of the patient, to guide the distal tip of the guiding catheter into the ostium. A balloon dilatation catheter may then be advanced through the guiding catheter into the patient's coronary artery until the balloon on the dilatation catheter is disposed within the stenotic region of the patient's artery. The balloon is inflated one or more times to open up the arterial passageway.

One type of catheter frequently used in PTCA procedures is an over-the-wire type balloon dilatation catheter. Commercially available over-the-wire type dilatation catheters include the SIMPSON ULTRA LOW PROFILE ®, the HARTZLER ACX ®, the HARTZLER ACX II ®, the PINKERTON 0.018 ™ and the ACS TEN ™ balloon dilatation catheters sold by the assignee of the present invention, Advanced Cardiovascular Systems, Inc. (ACS). When using an over-the-wire dilatation catheter, a guidewire is usually inserted into an inner lumen of the dilatation catheter before it is introduced into the patient's vascular system and then both are introduced into and advanced through the guiding catheter to its distal tip which is seated within the ostium of the desired coronary artery. The guidewire is first advanced out the seated distal tip of the guiding catheter into the desired coronary artery until the distal end of the guidewire extends beyond the lesion to be dilatated. The dilatation catheter is then advanced out of the distal tip of the guiding catheter into the patient's coronary artery, over the previously advanced guidewire, until the balloon on the distal extremity of the dilatation catheter is properly positioned across the lesion to be dilatated. Once properly positioned across the stenosis, the balloon is inflated to a predetermined diameter with radiopaque liquid at relatively high pressures (e.g., generally 4-12 atmospheres) to dilate the stenosed region of a diseased artery. After the dilatation, the balloon is deflated so that the dilatation catheter can be removed from the dilated stenosis and blood flow will resume therethrough.

Fixed-wire type dilatation catheter systems are also utilized very frequently in PTCA procedures. This type of dilatation catheter has a guidewire or guiding member secured within the catheter and provides a low profile, i.e. small transverse dimensions, because there is no inner tubular member which is characteristic of a commercially available over-the-wire dilatation catheter. Commercially available fixed-wire dilatation catheters include the HARTZLER EXCEL ®, the HARTZLER LPS ® and the SLALOM ™ dilatation catheters sold by ACS.

Another type of dilatation catheter, the rapid exchange type catheter, was introduced by ACS under the trademark ACS RX ® Coronary Dilatation Catheter. It is described and claimed in U.S. Pat. No. 5,040,548 (Yock), U.S. Pat. No. 5,061,273 (Yock) and U.S. Pat. No. 4,748,982 (Horzewski et al.) which are incorporated herein by reference. This dilatation catheter has a short guidewire receiving sleeve or inner lumen extending through a distal portion of the catheter. The sleeve or inner lumen extends proximally from a first guidewire port in the distal end of the catheter to a second guidewire port in the catheter spaced proximally from the inflatable member of the catheter. A slit may be provided in the wall of the catheter body which extends distally from the second guidewire port, preferably to a location proximal to the proximal end of the inflatable balloon. The structure of the catheter allows for the rapid exchange of the catheter without the need for an exchange wire or adding a guidewire extension to the proximal end of the guidewire. This catheter has been widely praised by the medical profession and it has met with much success in the market place because of the advantages of its unique design.

A recent improvement in the design and construction of fixed-wire dilatation catheters is disclosed in copending application Ser. No. 07/631,657 entitled FIXED WIRE CATHETER WITH ROTATABLE BALLOON ASSEMBLY which was filed on Dec. 21, 1990, and which is incorporated herein by reference. The fixed-wire catheter described in this copending application is provided with means to allow relative rotation between the balloon assembly and the core member of the guidewire so that the balloon will not wrap when the guidewire is torqued from its proximal end to guide the catheter as it is advanced through the patient's arterial system. This catheter design includes a sealing means which swells upon contacting the inflation liquid or other aqueous based liquids to prevent the passage of liquids through the seal. The structural integrity of the sealing means described in this reference depended to a large extent upon the core member or other inner member and this support usually precluded any significant longitudinal movement of the core member when the sealing means swelled in contact with an aqueous based liquid.

Another recent improvement in dilatation catheters is disclosed in copending application Ser. No. 07/809,888, filed Dec. 18, 1991, entitled INTRAVASCULAR CATHETER WITH MEANS TO SEAL GUIDEWIRE PORT, which includes a single lumen over-the-wire type catheter having a sealing means, such as a duck billed valve, on the distal end of the catheter and other locations thereon which seals against the guidewire or guiding member to prevent the loss of inflation liquid but which allows movement of the guidewire through the catheter in the same manner as in over-the-wire dilatation catheters. The single lumen is adapted to receive the guidewire and to direct inflation liquid to the interior of the dilatation balloon. The application is incorporated by reference into the present application.

What has been needed and heretofore unavailable is a sealing means which has adequate strength to be self supporting and to support a guidewire extending through the sealing means and which has sufficient lubricity to facilitate the movement of the core member or other inner member with respect to the dilatation balloon. The present invention satisfies these and other needs.

SUMMARY OF THE INVENTION

The present invention is directed to a sealing element for an elongated catheter for intraluminal procedures which facilitates relative movement between catheter parts.

The sealing element of the invention comprises a supporting matrix which has a bearing surface adapted to receive a movable member. Lubricous material, such as a hydrophilic polymer, which swells upon contact with an aqueous based liquid, is incorporated within at least the portion of the supporting matrix which defines the bearing surface. Upon contact with an aqueous based liquid, the lubricous material causes the polymer material defining the bearing surface to swell, thereby sealing the interface between the bearing surface and the movable member so as to prevent the passage of a significant amount of liquid therethrough. The lubricity provided by the lubricous material incorporated into the polymer matrix allows the movable member to readily move over the bearing surface, rotationally or linearly, when the swollen matrix presses against the surface of the movable member. In a presently preferred embodiment, the bearing surface defines a passageway through the sealing member which is adapted to receive the movable member.

The supporting matrix of the sealing element is preferably formed of a thermoplastic polymer, such as thermoplastic polyurethane, and the presently preferred thermoplastic polyurethane is TECOFLEX polyurethane sold by Thermedics Inc., Woburn, Mass. The incorporated lubricous material is preferably a hydrophilic polymer material such as polyacrylonitriles sold by Kingston Technology of Dayton, N.J. under the trademark HYDROPAN®, or a high molecular weight polyethylene oxide sold by Union Carbide Corporation under the trademark POLY-OX®. The presently preferred hydrophilic polymer is HYPAN SS201.

The sealing element is conveniently formed by mixing lubricous material with the matrix polymeric material in amounts of about one part (by weight) to about 1 to about 20 parts, preferably about 5 to about 15 parts of the matrix polymer. Up to about 5% (by weight) of plasticizer such as polyethylene glycol may be also incorporated into the matrix polymeric material to facilitate mixing the hydrophilic polymer with the matrix polymeric material. Other materials may also be incorporated into the matrix. It is preferred to first dissolve the polyurethane into a compatible solution such as tetrahydrofuran or methylene chloride and then add the hydrophilic lubricous material, plasticizer and other materials which are to be incorporated into the matrix. The mixture thickens after a thorough mixing of the components in a suitable mixer such as a flask or beaker. The thickened mixture is formed about a cylindrically shaped mandrel and then cured. The mandrel preferably has the exterior dimensions which are desired for the passageway through the matrix. The mixture is heated between about 50° C. and 75° C. for about 1 to about 4 hours to remove solvent and solidify. After solidification it may then be removed from the mandrel.

In one presently preferred embodiment, a guiding element or guidewire is disposed within the passageway of the sealing element. The passageway is dimensioned so as to provide a liquid tight seal when the material forming the passageway swells upon contact with an aqueous based liquid and seals against the guiding element or guidewire therein.

The sealing element provides excellent sealing of catheter components to prevent the loss of inflation liquid and allows easy movement of a catheter component such as a guidewire or guiding member within a passageway through the sealing element. These and other advantages of the invention will become more apparent from the following detailed description of the invention, when taken in conjunction with the accompanying exemplary drawings.

BRIEF DESCRIPTION OF THE DRAWINGS

FIG. 1 is an elevational view, partially insection, of a single lumen over-the-wire dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is an elevational view, partially in section, of a fixed-wire dilatation catheter with a rotatable balloon assembly embodying features of the invention.

FIG. 5 is a transverse cross-sectional view of the fixed-wire dilatation catheter shown in FIG. 4 taken along the lines 5—5.

FIG. 6 is a transverse cross-sectional view of the fixed-wire dilatation catheter shown in FIG. 4 taken along the lines 6—6.

FIG. 7 is a transverse cross-sectional view of the fixed-wire dilatation catheter shown in FIG. 4 taken along the lines 7—7.

DETAILED DESCRIPTION OF THE INVENTION

FIG. 1 illustrates a dilatation catheter 10 of the invention which includes a catheter shaft 11 having a single inner lumen 12, inflatable member 13 on a distal extremity of the catheter shaft which has an interior in fluid communication with the inner lumen 12 and an adapter 14 on the proximal end of the catheter shaft 11 which is adapted to introduce inflation liquid into the inner lumen 12. A sealing member 15 is secured within the inner lumen 12 by suitable means such as an adhesive to the interior of the extension 16 of the catheter shaft 11 which extends through the interior of the inflatable member 13. The proximal end of the inflatable member 13 is secured by suitable means such as heat bonding or an adhesive to the exterior of the catheter shaft 11 and the distal end of the inflatable member is secured by similar means to the distal end of the extension 16. A plurality of inflation ports 17 are provided in the portion of the extension 16 within the interior of the inflatable member 13 to direct inflation liquid into the interior. A radiopaque marker 18 is centrally disposed about the extension 16 to facilitate fluoroscopic observation of the balloon during an angioplasty procedure.

FIG. 2 depicts in transverse cross-section the catheter shaft 11, showing a hypotube 19 and a plastic jacket or coating 20 on the exterior of the hypotube.

The sealing member 15, as shown in FIGS. 3 and 4, is generally tubular in shape with an inner passageway 21 extending therethrough 15 which slidably receives guidewire 22.

The catheter 10 may be advanced to a desired location within a patient's arterial system utilizing conventional techniques for over-the-wire balloon angioplasty catheters. To facilitate the placement of the catheter, a guiding catheter (not shown) having a preshaped distal tip is first percutaneously introduced into the cardiovascular system of a patient by means of the Seldinger technique through the brachial or femoral arteries. The guiding catheter is advanced therein until its preshaped distal tip is disposed within the aorta adjacent the ostium of the desired coronary artery. The guiding catheter is twisted or torqued from its proximal end, which extends out of the patient, to guide its distal tip into the ostium of the desired coronary artery. Guidewire 22 is usually inserted into the guidewire receiving inner lumen 12 of the catheter shaft 11 before the catheter 10 is introduced into the patient's vascular system and then both the guidewire and the catheter are introduced into and advanced through the guiding catheter to its distal tip. The guidewire 22 is first advanced out the seated distal tip of the guiding catheter and through the desired coronary artery until the distal end of the guidewire extends beyond the lesion to be dilatated. The catheter 10 is then advanced out of the distal tip of the guiding catheter, over the previously advanced guidewire 22, until the inflatable member 13 on the distal extremity of catheter 10 are properly positioned across the lesion to be dilatated in the coronary artery.

Once the inflatable member 13 is properly positioned across the lesion, inflation fluid is directed through the arm 23 of adapter 14 into the single inner lumen 12 of the catheter shaft 11 to the interior of the inflatable member 13 in order to perform a dilatation. The fitting between the guidewire 22 and the sealing member 15 prior to entering the body lumen is relatively loose. However, upon contact with an aqueous based liquid, whether it be inflation liquid, blood or other fluid, the diameter of the passageway 21 of the sealing member 15 shrinks due to the expansion of the lubricous material incorporated into the matrix forming the sealing member which causes the inner surface of the passageway 21 to sealingly engage the surface of the guidewire 22 and prevent the passage of liquid through the interface between the surface of the passageway and the surface of the guidewire. However, the lubricous nature of the lubricous component incorporated into the polymer matrix of sealing member 15 ensures that the guidewire 22 readily moves within the passageway 21 even though the inner surface of the sealing member which defines the passageway tightly engages the guidewire surface to prevent the passage of liquid.

FIGS. 5-7 illustrate a fixed-wire dilatation catheter 30 embodying features of the invention, which generally includes an elongated torquable shaft 31, a guide member 32 joined at the proximal end 33 thereof to the distal end 34 of the torquable shaft 31 and a balloon assembly 35 comprising a balloon 36 and a tubular extension 37. The balloon assembly 35 is mounted about the distal section 38 of the torquable shaft 31 so that it is freely rotatable with respect to the torquable shaft and the guide member 32.

A flexible coil 40 having a rounded plug 41 on the distal end thereof is disposed about and secured to the portion of the guide member 32 which extends out the distal end of the balloon 36 at a suitable location 42 distally of the balloon 36.

A removable hub 43, such as the Luer lock shown, is connected to the proximal end of the elongated torquable shaft 31 to facilitate connection to a source for radiopaque inflation fluid. The torquing knob 44 on the proximal end of the torquable shaft 31 permits the torquing of the catheter when it is advanced through a patient's vasculature.

The elongated torquable shaft 31 is preferably hypotubing formed from stainless steel, such as type 304 stainless steel, or other suitable materials such as Nitinol which has been thermomechanically processed to have superelastic properties at body temperature. The shaft 31 has a main tubular section 45 and a smaller diameter, more flexible distal section 38 and has an inner lumen 46 extending through both tubular sections. The distal tubular section 38 has one or more inflation ports 47 therein to direct inflation fluid from the inner lumen 46 into the interior of the balloon 36 for the inflation thereof. Inflation fluid is introduced into the inner lumen 46 at the proximal end of the torquable shaft through hub 43.

Typical dimensions of the torquable shaft 31 include an overall length of about 135 to about 145 cm. The main section 45 of the torquable shaft 31 has an outside diameter of about 0.018 inch (0.457 mm), an inside diameter of about 0.012 inch (0.305 mm) and a length of about 90 to about 120 cm. The small diameter distal section 38 of torquable shaft 31 has an outside diameter of about 0.012 inch (0.305 mm), an inner diameter of about 0.008 inch (0.203 mm) and a length of about 10 to about 15 cm. The distal section 38 is seated within the distal end of the main tubular section 45 and secured therein by suitable adhesive such as Loctite TM. The torquable member 31 is provided with sequentially smaller diameters toward the distal end thereof to increase the flexibility thereof. These smaller diameter sections can be formed by joining sections of tubing having sequentially smaller diameters, as shown in the FIG. 1 or they can be formed by drawing the tubular sections of the torquable member 31 with sequentially smaller outer diameters. The inflation ports 47 in the smaller diameter distal section 38 have a diameter of about 0.003 inch (0.076 mm) and are formed with a MS35 YAG laser.

The proximal end of the guide member 32 is suitably secured about 3 to 4 mm within the distal end of the main tubular section 45 by welding. The guide member 32 is about 25 to about 40 cm in length and tapers in the distal direction to smaller diameters to provide greater flexibility to the distal end of the catheter 30. In the presently preferred embodiment, the first taper is about 5–7 mm long and reduces the outer diameter from about 0.007 to about 0.006 inch (0.178–0.152 mm) and the second taper is about 2.0 to 2.5 cm long and has a reduction in diameter of from 0.006 to about 0.0025 inch (0.152–0.064 mm). The most distal portion 48 of guide member 32 is preferably flattened to a rectangular transverse cross section of about 0.001 by 0.003 inch (0.025–0.076 mm) to provide even greater flexibility in a single plane and also to facilitate the manual shaping thereof which is necessary to be able to steer the catheter through the patient's arteries. The guide member 32 may be in the form of a solid rod or a hollow tube.

The coil 40 is secured to the guide member 32 at location 42 by suitable means such as brazing or soldering. The wire from which the coil 40 is formed is about 0.0025 inch (0.064 mm) in diameter and is preferably formed of a palladium-platinum-molybdenum alloy. The plug 41 generally is formed by welding the distal tip of the guide member 32 to the distal end of the coil 40 and is rounded to minimize arterial damage as the catheter is advanced through a patient's vascular system.

In the balloon assembly 35, the proximal end of the balloon 36 is adhesively secured to the distal end of the tubular extension 37. The proximal end of tubular extension 37 extends proximally beyond the inflation ports 47 and is secured to the distal end of main tubular member 45. An annular sealing element 50, which is preferably secured by a suitable adhesive to the inside of the tubular extension 37, has an inner passageway 51 through which the small diameter distal section 38 is slidably disposed. A similar annular sealing element 52, which is also preferably secured by a suitable adhesive to the inside of the distal end of the balloon 36, has a passageway 53 through which the which the guide member 32 is slidably disposed. The sealing members 50 and 52 generally comprise a polymer matrices which have bearing surfaces within the passageways 51 and 53 and which have incorporated within at least the portion of the matrices which form the bearing surfaces lubricous material which swells upon contact with the aqueous based inflation fluid so as to sealingly engage the surface of the distal section 38 of shaft 31 and the surface of guiding member 32. The lubricity of this incorporated material allows relative rotational movement between the balloon assembly 35 and the torquable shaft 31 and guiding member 32. Moreover, these sealing elements also seal the proximal and distal ends of the balloon assembly 35 to prevent significant loss of inflation liquid during balloon inflation, even at pressures of up to 12 atmospheres or more. Suitable materials for the sealing elements have been described in the prior embodiment.

Air readily passes through the interface between the passageways 51 and 53 and the surfaces of the tubular distal section 38 and the distal portion of the guide member 32, so that any air trapped within the interior of the balloon 36 will be driven through the interfaces when the balloon is inflated with the aqueous based inflation fluid. However, as soon as the aqueous-based inflation fluid contacts the hydrophilic material incorporated within the matrices of the sealing members 50 and 52, it swells, pressing the bearing surfaces against the movable members within the passageways 51 and 53, thereby blocking off the further passage of the aqueous-based liquid.

A bearing 56 is rotatably mounted on the distal tubular section 38 between the raised projections or stops 57 which restrict the relative axial movement of the bearing. The outer diameter of the bearing 56 is secured to the inside of the tubular extension 37 by means of an adhesive such as Loctite FMD-13.

An alternate embodiment having a distal construction commonly identified as a floppy design (not shown) may be used. In this embodiment the distal end of the guide element 32 would not extend to the distal end of the coil 40, but instead it would be joined to the coil at an intermediate location and a shaping ribbon would extend from the brazement at the intermediate location to the plug 41. The ribbon is usually manually bent or curved to facilitate the steering of the distal end of the catheter into a desired blood vessel during angioplasty procedures. In a presently preferred embodiment, the shaping ribbon is formed of material stronger than the material of the guide member 32 such as tungsten or tungsten alloys and it has typical transverse cross-sectional dimensions of about 0.001×0.003 inch (0.025×0.076 mm).

While the present invention has been described herein in terms of certain presently preferred catheters, it can be used in a variety of catheter designs. Modifications and improvements may be made without departing from the scope of the invention.

What is claimed is:

1. An intravascular catheter assembly comprising:
   a) an elongated catheter shaft having an inner lumen extending therein and a distal end for vascular insertion
   b) a movable guiding member disposed within the inner lumen in the catheter shaft; and
   c) a sealing element disposed within a distal portion of the catheter shaft between the inner lumen and the movable guiding member which has a bearing surface configured to slidably receive the movable member, the portion of the sealing element forming the bearing surface having incorporated therein a lubricous material which swells upon contact with an aqueous based liquid so as to cause the bearing surface to sealingly engage the movable guiding member and which facilitates relative movement between the surface of the movable member and the bearing surface when there is sealing engagement therebetween.

2. The intravascular catheter of claim 1 wherein the sealing element is formed of a thermoplastic polymer.

3. The intravascular catheter of claim 2 wherein the lubricous material is hydrophilic.

4. The intravascular catheter of claim 3 wherein the lubricous material is selected from the group consisting of polyacrylonitrile and a high molecular weight polyethylene oxide.

5. The intravascular catheter of claim 1 wherein the bearing surface of the sealing element defines a passageway through the sealing element which is adapted to receive the movable member.

6. A dilatation catheter for angioplasty procedures comprising:
   a) an elongated catheter shaft having proximal and distal ends and an inner lumen extending therein to the distal end;
   b) an inflatable member on a distal portion of the catheter shaft proximal to the distal end of the catheter shaft having an interior in fluid communication with the inner lumen extending within the catheter shaft;
   c) a tubular member which forms at least part of the distal portion of the catheter shaft, which has a portion of the inner lumen extending therein and which extends through and distal to the inflatable member; and
   d) a sealing element secured within the distal portion of the catheter shaft distal to the inflatable member and having a bearing surface adapted to slidably engage a movable member disposed within the inner lumen, the portion of the sealing element forming the bearing surface having incorporated therein a lubricous material which swells upon contact with an aqueous based liquid so as to sealingly engage a surface of the movable member and which facilitates relative movement between the surface of the movable member and the bearing surface when there is sealing engagement therebetween.

7. The dilatation catheter of claim 6 wherein the sealing element is formed of a thermoplastic polymer.

8. The dilatation catheter of claim 6 wherein the lubricous material is hydrophilic.

9. The dilatation catheter of claim 6 wherein the lubricous material is selected from the group consisting of polyacrylonitrile and a high molecular weight polyethylene oxide.

10. The dilatation catheter of claim 6 wherein the bearing surface of the sealing element forms a passageway through the sealing element which is adapted to receive the movable member.

11. The intravascular catheter of claim 1 wherein the movable member is a guidewire.

* * * * *

UNITED STATES PATENT AND TRADEMARK OFFICE
CERTIFICATE OF CORRECTION

PATENT NO. : 5,348,537
DATED : September 20, 1994
INVENTOR(S) : Steven P. Wiesner et al.

It is certified that error appears in the above-identified patent and that said Letters Patent is hereby corrected as shown below:

In col. 4, line 28, Fig. "4" should be --Fig. 5--.

In col. 4, line 27, after the paragraph ending on line 27, insert

--Fig. 4 is a perspective view of the sealing member shown in Figs. 1 and 3.--

In col. 4, lines 31-33, "Fig. 5 to 5-5" should be deleted.

In col. 4, line 35, "Fig. 4" should be --Fig. 5--.

In col. 4, line 38, "Fig. 4" should be --Fig. 5--.

Signed and Sealed this

Eleventh Day of April, 1995

*Attest:*

BRUCE LEHMAN

*Attesting Officer*  *Commissioner of Patents and Trademarks*